(12) United States Patent
Brady et al.

(10) Patent No.: US 7,223,891 B2
(45) Date of Patent: May 29, 2007

(54) SOLID-PHASE PREPARATION OF [$^{18}$F] FLUOROHALOALKANES

(75) Inventors: Frank Brady, London (GB); Sajinder Kaur Luthra, London (GB); Yongjun Zhao, London (GB)

(73) Assignee: Hammersmith Imanet Ltd., London (GB)

( * ) Notice: Subject to any disclaimer, the term of this patent is extended or adjusted under 35 U.S.C. 154(b) by 0 days.

(21) Appl. No.: 10/539,163

(22) PCT Filed: Dec. 19, 2003

(86) PCT No.: PCT/GB03/05630

§ 371 (c)(1),
(2), (4) Date: Jun. 14, 2005

(87) PCT Pub. No.: WO2004/056726

PCT Pub. Date: Jul. 8, 2004

(65) Prior Publication Data

US 2006/0069294 A1 Mar. 30, 2006

(30) Foreign Application Priority Data

Dec. 20, 2002 (GB) .................................. 0229688.7

(51) Int. Cl.
C07C 17/00 (2006.01)
C07C 17/42 (2006.01)
(52) U.S. Cl. ...................................... 570/101; 570/106
(58) Field of Classification Search ................ 568/33; 570/101, 106
See application file for complete search history.

(56) References Cited

U.S. PATENT DOCUMENTS 6,486,354 B1   11/2002   Gani et al.

FOREIGN PATENT DOCUMENTS

| EP | 0030516 | 6/1981 |
|---|---|---|
| WO | 03/002157 | 1/2003 |
| WO | WO 3002157 A1 * | 1/2003 |

OTHER PUBLICATIONS

S. Comagic, M. Piel, R. Schirrmacher, S. Hohnemann, F. Rosch Efficient synthesis of 2-bromo-1-[18F]fluoroethane and its application in the automated preparation of 18F-fluoroethylated compounds Applied Radiation and Isotopes 56 (2002) 847-851.*
S. Comagic, M. Piel, R. Schirrmacher, S Hohnemann, F. Rosch Applied Research and Isotopes 56 (2002) 847-851.*
Chemical Abstract AN 1988:130967 of J. of Labelled Compounds and Radiopharm. (1987), vol. 24(9), pp. 1029-1042.
S. Comagic, et al., "Efficient Synthesis of 2-Bromor1- 18F-fluorethane and its Applicationin the Automated Preparation of 18F-Fluorethlated Compounds" Applied radiation and isotopes, vol. 56, 2002, pp. 847-851.
Search Report for GB 0229688.7 dated May 29, 2003.
Int'l Search report for PCT/GB2003/005630 dated May 4, 2004.
Int'l Preliminary Examination Report for PCT/GB2003/005630 dated Oct. 21, 2004.

* cited by examiner

*Primary Examiner*—Samuel A Barts
*Assistant Examiner*—Lalitha Nagubandi
(74) *Attorney, Agent, or Firm*—Li Cai

(57) ABSTRACT

The invention relates to a process for the production of an [$^{18}$F]fluorohaloalkane which comprises treatment of a solid support-bound precursor of formula (I): SOLID SUPPORT-LINKER-$SO_2$—O—$(CH_2)_n$X (I) wherein n is an integer of from (1) to (7) and X is chloro, bromo or iodo; with $^{18}F^-$ to produce the [$^{18}$F]fluorohaloalkane of formula (II) $^{18}$F—$(CH_2)_n$—X (II) wherein n and X are as defined for the compound of formula (I), optionally followed by (i) removal of excess $^{18}F^-$, for example by ion-exchange chromatography; and/or (ii) removal of organic solvent.

5 Claims, No Drawings

SOLID-PHASE PREPARATION OF [$^{18}$F] FLUOROHALOALKANES

This application is a filing under 35 U.S.C. 371 of international application number PCT/GB2003/005630, filed Dec. 19, 2003, which claims priority to application number 0229688.7 filed Dec. 20, 2002, in Great Britain the entire disclosure of which is hereby incorporated by reference.

The present invention relates to a process for the preparation of fluorohaloalkane compounds such as [$^{18}$F]bromofluoromethane. [$^{18}$F]Fluorohaloalkanes are important reagents for performing O—, N—, and S—[$^{18}$F]fluoroalkylations and are commonly used to radiolabel radioligands for use in positron emission tomography (PET) studies.

[$^{18}$F]Fluorohaloalkanes have previously been prepared by nucleophilic displacement, by [$^{18}$F]F$^-$, of a leaving group from a suitable precursor compound. Thus, for example Zhang et al, Applied Radiation and Isotopes 57, 335–342 (2002), describes synthesis of [$^{18}$F]fluoroethyl bromide by nucleophilic displacement of 2-trifluoromethanesulphonyloxy ethylbromide with [$^{18}$F]F$^-$ and Seung-Jun et al Applied Radiation and Isotopes (1999), 51, 293–7 describes an analogous synthesis of 3-[$^{18}$F]fluoropropylbromide. A similar method is described in Comagic et al Applied Radiation and Isotopes (2002), 56, 847–851 wherein 2-bromo-1-[$^{18}$F] fluoroethane is prepared by nucleophilic displacement of 1,2-dibromoethane with [$^{18}$F]F$^-$. Solid-phase nucleophilic fluorination methods are described in co-pending International Patent Application PCT/GB02/02505.

In view of the importance of [$^{18}$F]fluorohaloalkanes as radiolabelling reagents, there exists the need for synthetic methods for their preparation in good radiochemical yield and in which isolation of the product is more readily achievable. Furthermore, there is also a need for such synthetic methods which are amenable to automation.

In a first aspect, the invention provides a process for the production of an [$^{18}$F]fluorohaloalkane which comprises treatment of a solid support-bound precursor of formula (I):

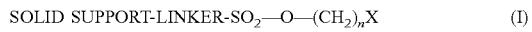

SOLID SUPPORT-LINKER-SO$_2$—O—(CH$_2$)$_n$X     (I)

wherein n is an integer of from 1 to 7 and X is chloro, bromo, or iodo;

with $^{18}$F$^-$ to produce the [$^{18}$F]fluorohaloalkane of formula (II)

$^{18}$F—(CH$_2$)$_n$—X     (II)

wherein n and X are as defined for the compound of formula (I), optionally followed by
(i) removal of excess $^{18}$F$^-$, for example by ion-exchange chromatography; and/or
(ii) removal of organic solvent.

Preferably, in the compounds of formula (I) above, n is an integer of 1 to 4, more preferably, 1 or 2. In the compounds of formula (I) above, X is preferably bromo or iodo. Preferred [$^{18}$F]fluorohaloalkanes of formula (II) prepared, include [$^{18}$F]fluorobromomethane, [$^{18}$F]fluoroiodomethane, [$^{18}$F]fluorobromoethane, [$^{18}$F]fluoroiodoethane, [$^{18}$F]fluorobromopropane, and [$^{18}$F]fluoroiodopropane.

As the [$^{18}$F]fluorohaloalkane of formula (II) is removed from the solid-phase into solution, all unreacted precursor remains bound to the resin and can be separated by simple filtration, thus obviating the need for complicated purification, for example by HPLC. The [$^{18}$F]fluorohaloalkane of formula (II) may be cleaned up by removal of excess F$^-$, for example by ion-exchange chromatography and/or by removal of any organic solvent.

As shown in Scheme 1, the compound of formula (I) may be conveniently prepared from any sulphonic acid functionalised commercially available resin, such as Merrifield Resin, NovaSyn® TG Bromo Resin, (Bromomethyl)phenoxymethyl polystyrene, or Wang Resin which may be reacted with a chlorinating agent to give the corresponding sulphonyl chloride resin. This may be carried out by treating the resin with, for example, phosphorus pentachloride, phosphorus trichloride, oxalyl chloride, or thionyl chloride, in an appropriate inert solvent such as dichloromethane, chloroform, or acetonitrile, and heating at elevated temperature for a period of time. The excess reagent may then be removed from the resin by washing with further portions of the inert solvent. The sulphonyl chloride resin may then be reacted with the alcohol analogue of the tracer to produce the resin-bound precursor of formula (I). This may be carried out by treating the resin with a solution of the alcohol in an inert solvent such as chloroform, dichloromethane, acetonitrile, or tetrahydrofuran containing a non-nucleophilic soluble base such as sodium hydride or a trialkylamine, for example triethylamine or diisopropylethylamine. The reaction may be carried out at a temperature of 10 to 80° C., optimally at ambient temperature for a period of from around 1 to 24 hours. The excess alcohol and base may then be removed from the solid support by washing with further portions of an inert solvent such as chloroform, dichloromethane, or tetrahydrofuran. Alternatively, the LINKER may be attached to the haloalkane, before being attached to the SOLID SUPPORT to form the compound of formula (I), using analogous chemistry to that described above.

Scheme 1

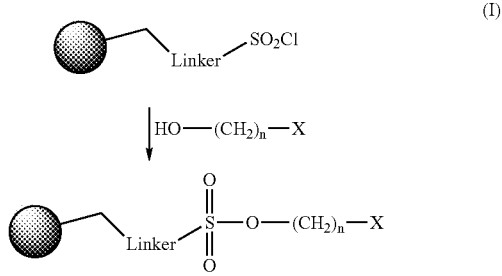

In the compounds of formula (I), the "SOLID SUPPORT" may be any suitable solid-phase support which is insoluble in any solvents to be used in the process but to which the LINKER and/or haloalkane can be covalently bound. Examples of suitable SOLID SUPPORT include polymers such as polystyrene (which may be block grafted, for example with polyethylene glycol), polyacrylamide, or polypropylene or glass or silicon coated with such a polymer. The solid support may be in the form of small discrete particles such as beads or pins, or as a coating on the inner surface of a cartridge or on a microfabricated vessel.

In the compounds of formula (I), the "LINKER" may be any suitable organic group which serves to space the reactive site sufficiently from the solid support structure so as to maximise reactivity. Suitably, the LINKER comprises zero to four aryl groups (suitably phenyl) and/or a C$_{1-16}$alkyl (suitably C$_{1-6}$alkyl) or C$_{1-16}$haloalkyl (suitably C$_{1-6}$haloalkyl), typically C$_{1-16}$ fluoroalkyl (suitably C$_{1-6}$ fluoroalkyl), or C$_{1-16}$alkoxy or C$_{1-16}$haloalkoxy (suitably $C_{1-6}$alkoxy or $C_{1-6}$haloalkoxy) typically $C_{1-16}$fluoroalkoxy (suitably $C_{1-6}$fluoroalkoxy), and optionally one to four additional functional groups such as amide or sulphonamide groups. Examples of such linkers are well known to those skilled in the art of solid-phase chemistry, but include:

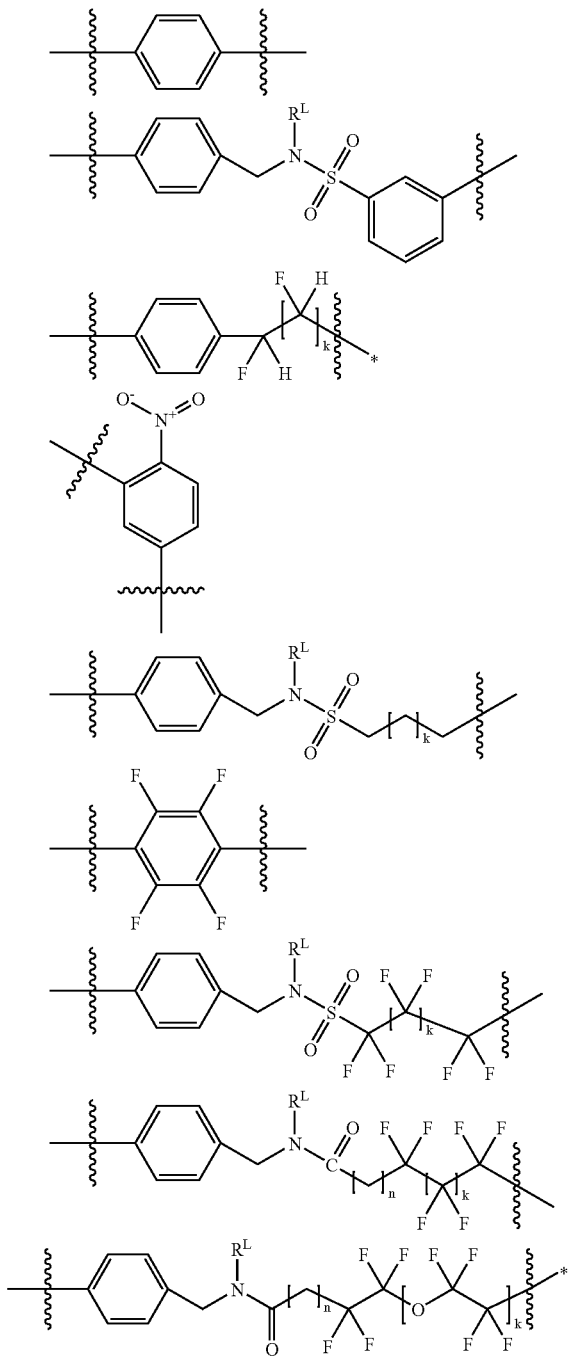

wherein at each occurrence, k is an integer of 0 to 3, n is an integer of 1 to 16, and $R^L$ is hydrogen or $C_{1-6}$ alkyl.

Treatment of the compound of formula (I) with $^{18}F^-$ may be effected by treatment with any suitable source of $^{18}F^-$, such as $Na^{18}F$, $K^{18}F$, $Cs^{18}F$, tetraalkylammonium $^{18}F$ fluoride, or tetraalkylphosphonium $^{18}F$ fluoride. To increase the reactivity of the fluoride, a phase transfer catalyst such as 4,7,13,16,21,24 hexaoxa-1,10-diazabicyclo[8,8,8] hexacosane may be added and the reaction performed in a non protic solvent. These conditions give reactive fluoride ions. The treatment with $^{18}F^-$ is suitably effected in the presence of a suitable organic solvent such as acetonitrile, dimethylformamide, dimethylsulphoxide, tetrahydrofuran, dioxan, 1,2 dimethoxyethane, sulpholane, N-methylpyrolidinineone, at a non-extreme temperature, for example, 15° C. to 180° C., preferably at elevated temperature. On completion of the reaction, the [$^{18}F$]fluorohaloalkane of formula (II) dissolved in the solvent is conveniently separated from the solid-phase by filtration.

Any excess $^{18}F^-$ may be removed from the solution of [$^{18}F$]fluorohaloalkane by any suitable means, for example by ion-exchange chromatography or solid phase absorbents. Suitable ion-exchange resins include BIO-RAD AG 1-X8 or Waters QMA and suitable solid phase absorbents include alumina. The excess $^{18}F^-$ may be removed using such solid phases at room temperature in aprotic solvents.

Any organic solvent may be removed by any standard method such as by evaporation at elevated temperature in vacuo or by passing a stream of inert gas such as nitrogen or argon over the solution.

According to a further aspect, the invention provides a process for the production of an [$^{18}F$]fluorohaloalkane which comprises treatment of a solid support-bound precursor of formula (III):

$$\text{SOLID SUPPORT-LINKER-I}^+\text{—(CH}_2)_n\text{X} \qquad \text{Y}^- \qquad (III)$$

wherein n and X are as defined for the compound of formula (I), and $Y^-$ is an anion (preferably trifluoromethylsulphonate (triflate) anion or tetraphenyl borate anion);

with $^{18}F^-$ to produce the [$^{18}F$]fluorohaloalkane of formula (II)

$$^{18}F\text{—(CH}_2)_n\text{—X} \qquad (II)$$

wherein n and X are as defined for the compound of formula (III), optionally followed by (i) removal of excess $^{18}F^-$, for example by ion-exchange chromatography; and/or (ii) removal of organic solvent.

The compound of formula (III) may be conveniently prepared from a functionalised commercially available resin such as a Merrifield Resin or Wang Resin. Suitably, a hydroxylodoaryl (such as an iodophenol) containing LINKER group is treated with an inorganic base, such as cesium carbonate and then added to the resin, pre-swollen with an inert solvent, such as N,N-dimethylformamide and allowed to react at elevated temperature, for example 30 to 80° C. Excess reagents may be removed by washing the resin with further inert solvent. The resultant iodophenol functionalised resin may then be treated with a source of acetate anions (such as actetic acid, acetic anhydride, or acetyl chloride) in the presence of an oxidising agent, such as hydrogen peroxide to provide the corresponding diacetoxy-iodophenyl functionalised resin. The diacetoxy-iodophenyl functionalised resin may then be stirred in an inert solvent, such as dichloromethane, in the presence of acid such as hydrochloric acid, trifluoromethane sulphonic acid, or acetic acid at a low temperature, suitably −40° C. to 10° C. before addition of the fluorohaloalkane, suitably functionalised as a boronic acid or triorgano tin (suitably trialkyl tin) derivative which may be coupled to the resin at a non-extreme temperature. As in previous steps, the desired compound of formula (III) may be separated by filtration and washing with an inert solvent.

In the compound of formula (III), the LINKER is as defined above but suitably comprises an aryl group (suitably phenyl) adjacent to the I+. Preferred examples include:

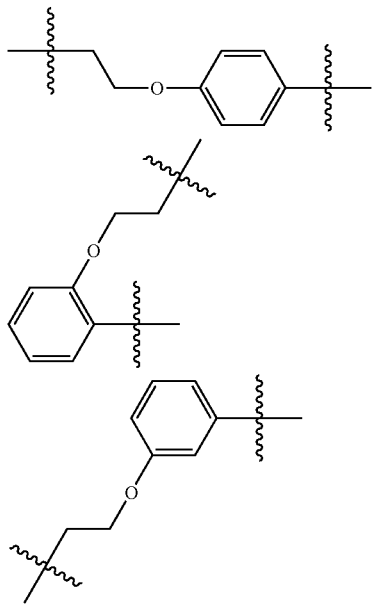

wherein each phenyl is optionally substituted by 1 to 4 groups selected from $C_{1-6}$alkyl and $C_{1-6}$alkoxy, but is suitably unsubstituted.

Treatment of a compound of formula (III) with $F^-$, preferred haloalkanes in formula (III), removal of excess $F^-$ and any organic solvent are all suitably as described for the compounds of formula (I) above.

The compounds of formula (I) and (III) are novel and thus form a further aspect of the present invention.

As described above, the advantages of such solid-phase processes for preparation of [$^{18}$F]fluorohaloalkanes include the relative speed of the process, simplified purification methods and ease of automation—all of which mean that the processes are suitable for preparation of [$^{18}$F]fluorohaloalkanes which can then be used to prepared $^{18}$F-labelled tracers for use in PET. Accordingly, the present invention provides a process for the preparation of a [$^{18}$F]fluorohaloalkane of formula (II) for use in PET chemistry.

Conveniently, the solid support bound precursor of formula (I) or (III) could be provided as part of a kit to a radiopharmacy, PET centre, or nuclear medicine department. The kit may contain a cartridge which can be plugged into a suitably adapted automated synthesiser. The cartridge may contain, apart from the solid support-bound precursor, a column to remove unwanted fluoride ion, and an appropriate vessel connected so as to allow the reaction mixture to be evaporated and allow the product to be formulated as required. The reagents and solvents and other consumables required for the synthesis may also be included together with a compact disc carrying the software which allows the synthesiser to be operated in a way so as to meet the customers requirements for radioactive concentration, volumes, time of delivery etc.

Conveniently, all components of the kit are disposable to minimise the possibilities of contamination between runs and may be sterile and quality assured.

The invention further provides a radiosynthesis kit for the preparation of an [$^{18}$F]fluorohaloalkane for use in PET chemistry, which comprises:

(i) a vessel containing a compound of formula (I) or (III); and
(ii) means for eluting the vessel with a source of $^{18}$F$^-$; and
(iii) an ion-exchange cartridge for removal of excess $^{18}$F$^-$.

The invention further provides a cartridge for a radiosynthesis kit for the preparation of an [$^{18}$F]fluorohaloalkane for use in PET chemistry which comprises:

(i) a vessel containing a compound of formula (I) or (III); and
(ii) means for eluting the vessel with a source of $^{18}$F$^-$.

The invention will now be illustrated by way of the, following Examples.

EXAMPLE 1

Synthesis of [$^{18}$F]-fluorobromomethane

EXAMPLE 1(i)

Preparation of perfluorobutane-1,4-bis-sulphonylchloride (Following the method of Weiming Qiu and Donald J. Burton Journal of fluorine chemistry, 60 (1993) 93–100.)

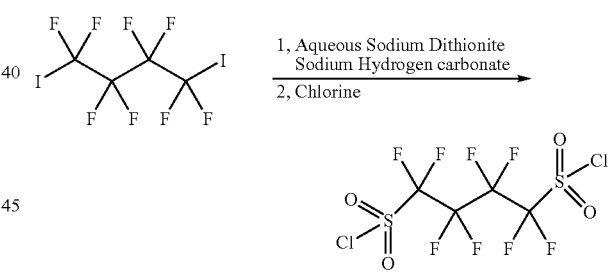

The mixture of 1,4 diiodoperfluorobutane (I(CF$_2$)$_4$I) (24.14 g, 53.2 mmol), sodium dithionite Na$_2$S$_2$O$_4$ (24 g, 117.2 mmol) and sodium hydrogen sulphate NaHCO$_3$ (12.8 g, 152.4 mmol) in water H$_2$O (36 ml)/Acetonitrile CH$_3$CN (36 ml) was stirred at room temperature for 2 hours. It was filtered, and the filtrate was concentrated under reduced pressure to remove the acetonitrile. To the residue was added H$_2$O (100 ml). The so obtained solution was vigorously stirred and treated with chlorine gas Cl$_2$ at 0° C. until the colour of I$_2$ disappeared. Dichloromethane CH$_2$Cl$_2$ (100 ml) was added and the mixture vigorously shaken. The organic phase was separated, and the aqueous phase was extracted with CH$_2$Cl$_2$. The combined organic phase was washed with water H$_2$O, brine, and dried with sodium sulphate Na$_2$SO$_4$ and concentrated to afford a waxy yellow crystalline solid. (15.4 g, 74%). Recrystallization from hexane afforded offwhite needles of perfluorobutane-1,4-bis-sulphonylchloride.

$^{19}$F NMR (CDCl$_3$, CFCl$_3$ reference) δ: –104.4, –119.1.

EXAMPLE 1(ii)

Preparation of perfluorobutane-1,4-bis-sulphonate dipotassium salt

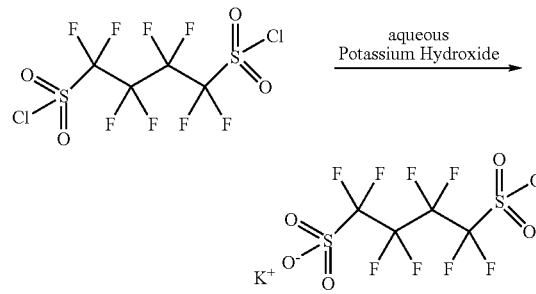

To the solution of potassium hydroxide KOH (9.8 g, 5 eq) in water H$_2$O (19 ml) was added gradually perfluorobutane-1,4-bis-sulphonylchloride (14 g, 35 mmol) at 85° C.–90° C. with stirring. After the addition, the reaction was continued for more 4 hours at the same temperature, and then it was cooled overnight. It was filtered and the solids was washed with a little of cooled water and dried in vacuum to give perfluorobutane-1,4-bis-sulphonate dipotassium salt $^{19}$F NMR (CD$_3$OD, CFCl$_3$ reference) δ: –114.00, –120.11.

EXAMPLE 1(iii)

Preparation of perfluorobutane-1,4-bis-sulphonic acid (Following the method described in U.S. Pat. No. 4,329,478, Fred E. Behr.)

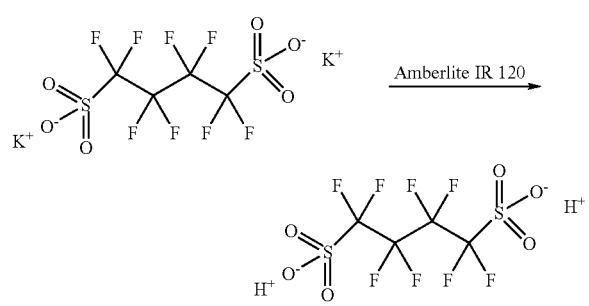

Perfluorobutane-1,4-bis-sulphonate dipotassium salt (15 g, 34.2 mmol) was dissolved in hot water (100 ml). It was added to an ion exchange column of Amberlyst 15 resin, (40×4 cm) which had been previously washed with excess 6N HCl and rinsed with distilled water. The column was then washed slowly with distilled water, and the first 300 ml of aqueous solution collected. The solution was concentrated in vacuum and the residue was dried under reduced pressure at 80° C. to afford perfluorobutane-1,4-bis-sulphonic acid. (11.0 g, 30 mmol, 88%)

$^{1}$H NMR (CDCl$_3$,) δ: 8.00

$^{18}$F NMR (CDCl$_3$, CFCl$_3$ reference) δ: –114.7, –121.3.

EXAMPLE 1(iv)

Preparation of perfluorobutane-1,4-bis-sulphonic acid anhydride (Following the method described in U.S. Pat. No. 4,329,478, Fred E. Behr.)

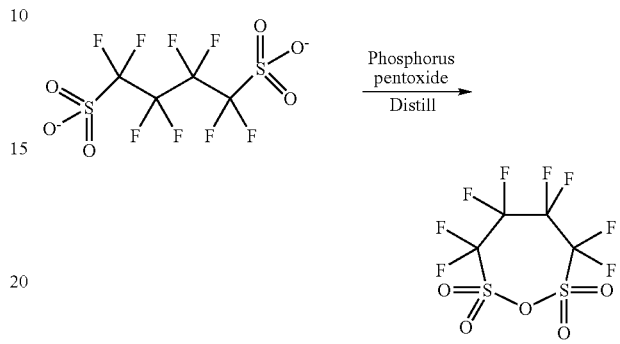

Perfluorobutane-1,4-bis-sulphonic acid (11.0 g, ~30 mmol) was mixed with P$_2$O$_5$ (40 g, ~10 eq) and sand. The mixture was heated to 140–180° C. and distilled under reduced pressure with dry-ice cooling collector to afford crude product (5.12 g). Redistilation gives pure perfluorobutane-1,4-bis-sulphonic acid anhydride.

$^{18}$F NMR (CDCl$_3$, CFCl$_3$ reference) δ: –105.7, –121.8.

EXAMPLE 1(v)

Synthesis of PS-4-(Benzyl-ethyl-sulfonamide)octafluoro-butane-1-sulfonic acid

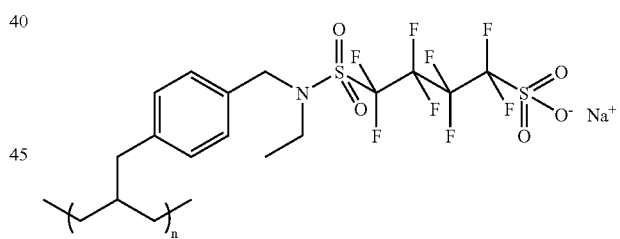

To a portion of the polystyrene resin (Novabiochem, Novasyn resin) (202 mg), which had previously been swollen in dichloromethane (2 ml) and then suspended in a further aliquot of dichloromethane (2 ml) the perfluorobutyl-1,4-cyclic-sulfonic anyhydride (116 mg, 5 Eq) was added. Following this di-isopropyethyl amine (0.174 ml) was added and the suspension stirred overnight at room temperature. The solvent was removed by filtration and the resin washed with consecutive addition and filtration of dichloromethane (5 ml), methanol (5 ml), DMF (5 ml), water (5 ml), methanol (5 ml), and dichloromethane (5 ml). The resulting resin was then treated with NaOH (1M) in THF/water (2×2 ml) before washing with consecutive portions of methanol (5 ml), dichloromethane (5 ml) and methanol (5 ml) again. The resin was then dried under high vacuum.

Gel Phase $^{19}$F NMR (referenced to CFCl$_3$,300K): δ–121.0, –114.8, –113.4

EXAMPLE 1(vi)

Synthesis of PS-4-(Benzyl-ethyl-sulfonamide)octafluoro-butane-1-sulfonyl chloride

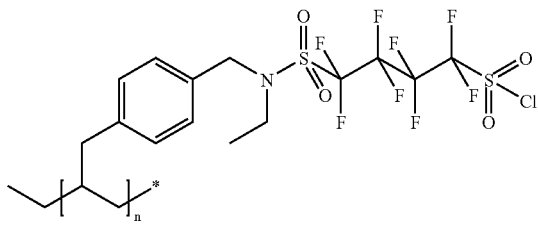

A portion of the resin prepared in the manner of Example 1(v) above is swollen with dichloromethane (2 ml) and then washed consecutively with HCl (1M) in THF/water (10×5 ml) to give the free sulphonic acid. The resin is washed consecutively with dichloromethane, methanol and THF before drying under high vacuum.

The resin is then suspended in dichloromethane and to it is added in excess a common chlorinating agent such as phosphorous pentachloride, phosphorus trichloride orthionyl chloride. The suspension is stirred for 2 hours before filtration and then washing of the resin with dichloromethane and then THF.

EXAMPLE 1(vii)

Synthesis of Fluorobromomethane Precursor Resin

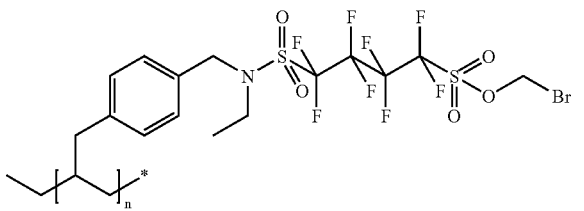

A solution of bromomethanol in THF is added to a portion of the resin prepared as described in Example 1(vi) above which has previously been swollen in THF. To this is added a solution of potassium t-butoxide in tetrahydrofuran and the suspension is stirred overnight. After filtration the resin is washed consecutively with dichloromethane and THF before drying under high vacuum.

EXAMPLE 1(viii)

Radiofluorination To Prepare [$^{18}$F]-fluorobromomethane

To a portion of the resin (prepared as described in Example 1(vii)) held in a cartridge is added a solution in dry acetonitrile of kryptofix, potassium carbonate and [$^{18}$F]-fluoride. The suspension is heated to 85° C. for 10 minutes and then the solution is filtered off. The solution is then passed onto a $C_{18}$ solid phase extraction cartridge and washed with water to remove acetonitrile, kryptofix and potassium carbonate. Addition of more acetonitrile washes the radiofluorinated product of the cartridge into a solution of 0.1 M HCl. This solution is heated for 5 minutes before neutralization and analysis.

What is claimed is:

1. A process for the production of an [$^{18}$F]fluorohaloalkane which comprises treatment of a solid support-bound precursor of formula (I):

SOLID SUPPORT-LINKER-SO$_2$—O—(CH$_2$)$_n$X    (I)

wherein n is an integer of from 1 to 7 and X is chloro, bromo or iodo; with a source of $^{18}$F$^-$ in an organic solvent and optionally in the presence of a phase transfer catalyst to produce the [$^{18}$F]fluorohaloalkane of formula (II)

$^{18}$F—(CH$_2$)$_n$—X    (II)

wherein n and X are as defined for the compound of formula (I), optionally followed by
(i) removal of excess $^{18}$F$^-$; and/or
(ii) removal of organic solvent.

2. A process for the production of an [$^{18}$F]fluorohaloalkane according to claim 1 wherein n is an integer of 1 to 4.

3. A process for the production of an [$^{18}$F]fluorohaloalkane according to claim 1 wherein the compound of formula (II) prepared is selected from [$^{18}$F]fluorobromomethane, [$^{18}$F]fluoroiodomethane, [$^{18}$F]fluorobromoethane, [$^{18}$F]fluoroiodoethane, [$^{18}$F]fluorobromopropane, and [$^{18}$F]fluoroiodopropane.

4. A process for the production of an [$^{18}$F]fluorohaloalkane according to claim 1 wherein the source of $^{18}$F$^-$ is selected from Na$^{18}$F, K$^{18}$F, Cs$^{18}$F, tetraalkylammonium $^{18}$F fluoride, and tetraalkylphosphonium $^{18}$F fluoride.

5. A process for the production of an [$^{18}$F]fluorohaloalkane according to claim 3 wherein n is an integer of 1 or 2.

\* \* \* \* \*